(12) United States Patent
Volz et al.

(10) Patent No.: US 7,417,015 B2
(45) Date of Patent: Aug. 26, 2008

(54) MASSAGING BAR SOAP

(75) Inventors: Elizabeth Volz, Princeton, NJ (US); Melissa Kuzmich, Somerville, NJ (US)

(73) Assignee: Colgate - Palmolive Company, New York, NY (US)

( * ) Notice: Subject to any disclaimer, the term of this patent is extended or adjusted under 35 U.S.C. 154(b) by 24 days.

(21) Appl. No.: 11/153,845

(22) Filed: Jun. 15, 2005

(65) Prior Publication Data

US 2005/0282717 A1   Dec. 22, 2005

Related U.S. Application Data

(60) Provisional application No. 60/580,305, filed on Jun. 16, 2004.

(51) Int. Cl.
*A61K 7/50* (2006.01)

(52) U.S. Cl. .............. 510/141; 510/146; 510/152; 510/153

(58) Field of Classification Search .............. None
See application file for complete search history.

(56) References Cited

U.S. PATENT DOCUMENTS

| 3,884,605 A | 5/1975 | Grelon |
| 5,602,088 A | 2/1997 | Tokosh et al. |
| 5,834,410 A | 11/1998 | Slocum |
| 6,383,999 B1 | 5/2002 | Coyle et al. |
| 6,723,690 B1 | 4/2004 | Aronson et al. |
| 6,727,211 B1 | 4/2004 | Aronson et al. |
| 6,730,642 B1 | 5/2004 | Aronson et al. |

FOREIGN PATENT DOCUMENTS

GB    1142238    2/1969

*Primary Examiner*—Necholus Ogden

(57) ABSTRACT

A soap bar comprising at least two different portions wherein the portions have a difference in solubility of at least 1.0%.

2 Claims, No Drawings

MASSAGING BAR SOAP

CROSS-REFERENCE TO RELATED APPLICATIONS

This application claims benefit of U.S. Provisional Application No. 60/580,305, filed Jun. 16, 2004, the disclosure of which is hereby incorporated herein by reference in its entirety.

FIELD OF THE INVENTION

This invention relates to a bar soap that can provide massaging and, optionally, exfoliating benefits.

BACKGROUND OF THE INVENTION

Various bar aesthetics have been used in marketed products, especially bars having a striped or marbled appearance such as, for example, IRISH SPRING® bar soap from Colgate-Palmolive Co., COAST® Soap from Procter and Gamble, SKIN SO SOFT® by Avon, DOVE NUTRIUM® from Unilever and other specialty products including "Lavendel" from Kappus, a Germany product imported into the United States, and Apothary Stone Washed Refining Soap by Yardley London.

SUMMARY OF THE INVENTION

This invention comprises a bar soap having at least two different portions wherein the individual portions have a solubility difference in water of at least 1.0%, particularly in the range of 3.0-7.0%. Upon use of the bar, the differential in solubilities creates a ridged structure which is useful to provide a massaging and, optionally, an exfoliating effect.

DETAILED DESCRIPTION OF THE INVENTION

The bars of the invention comprise at least two different portions which may be in the form of separate stripes, separate discontinuous areas, or other portions of separateness of varying sizes and shapes. The bar has at least two portions each of which has a selected solubility so that the difference between the at least two portions is a minimum of 1.0% and preferably a maximum of 10.0%, more preferably 3.0-7.0%. It is also possible that a bar may be created with more than two portions, provided that at least two of the portions have the described difference in solubilities. Upon use in washing with water, the bar develops ridges or other areas of height differences such that it has a textured effect. The bar can then be used as a massaging and, optionally, an exfoliating cleansing product.

In particular, examples of the invention include bars where the two or more portions can independently:

a) be matched in color so that there is no visual differentiation;
b) be different colors so that the bar appears striped;
c) contain both transparent and opaque portions or both transparent or both opaque portions;
d) contain exfoliants in one or more of the portions;
e) contain the same or different exfoliants;
f) contain pearlizing agents in one or multiple portions;
g) contain moisturizing agents in one or multiple portions; and
h) contain other benefit or visual agents (such as beads for visual effect, beads or encapsulates with benefit agents, such as moisturizing beads, fragrance beads, etc.).

The products of this invention include bars made with two portions where the first portion "A" as a less soluble portion comprises:
(a) 75-90 weight % of a soap such as a sodium soap and particularly a tallowate, cocoate or palmitate soap (particularly 82.6% of an 80/20 tallow/coco soap);
(b) 0.1-5 weight % of one or more of a $C_{12}$-$C_{20}$ straight or branched chain fatty acid (particularly coconut or stearic acid) (particularly 1.1% of coconut or stearic acid);
(c) 0.5-1.2 weight % of a hardening agent selected from the group consisting of inorganic electrolytes (especially sodium chloride), propylene glycol, mixtures of sodium chloride with polyethylene glycol (for example, PEG-600), and mixtures of sodium chloride with at least one high melting point wax (for example, 40-60° C. as a melting point range) (with a particular hardening agent being sodium chloride, especially in an amount of 0.7%);
(d) water (for example, 8-16 weight %); and
(e) optionally one or more ingredients selected from the group consisting of:
  (i) an opacifying and/or pearlizing agent such as in an amount of 0-0.5 weight % of titanium dioxide, mica, coated mica, and mixtures thereof (particularly titanium dioxide such as in an amount of 0.3%);
  (ii) fragrance (such as in an amount of 0-2 weight %, particularly 1.2%);
  (iii) a preservative such as in amount of 0.02-0.1 weight % (particularly a chelating type of preservative such as pentasodium pentate or EDTA, especially 0.05% of pentasodium pentate);
  (iv) an antioxidant such as in an amount of 0.01-0.05 weight %, particularly tetradibutyl pentaerythrityl hydroxyhydrocinnamate or butylated hydroxytoluene ("BHT"); particularly 0.02% of tetradibutyl pentaerythrityl hydroxyhydrocinnamate;
  (v) a colorant such as in an amount of 0.001-0.1 weight %, particularly 0.002%;
  (vi) 0.1-5.0 weight % of a humectant or skin conditioner such as glycerin, petrolatum, mineral oil, silicone compounds waxes, natural oils (such as sunflower, olive, jojoba, sesame, safflower, wheat germ, almond, safflower, canola or avacado oils) shear butter, lanolin, vitamin E or mixtures thereof (particularly 2.3% glycerin); and
  (vii) exfoliating agents such as polyethylene beads, jojoba beads, oat flour, lufa or bran.

The second portion "B" as a more soluble portion comprises:
(a1) 60-75 weight % of a soap such as a sodium soap and particularly a tallowate, cocoate or palmitate soap (particularly 65.5% of an 80/20 tallow/coco soap);
(b1) a solubility enhancing component selected from the group consisting of
  (i) 6-10 weight % of a non-saccharide humectant such as glycerin (particularly 7.6% of glycerin);
  (ii) 3-10 weight % of an alcohol, for example, sorbitol or manitol (particularly 5.7% sorbitol);
  (iii) 0.5-10% of a saccharide type humectant, for example, sucrose, dextrose, fructose, glucose, xylitol, honey or lactose;
  (iv) 0.5-25 weight % of a non-soap synthetic surfactant (for example, cocamidopropyl betaine, sodium dodecyl benzene sulfonate, cocamide monoethanolamide, $C_6$-$C_{22}$ alkyl sulfosuccinates, and $C_8$-$C_{18}$ acyl isethionates, $C_8$-$C_{22}$ sarconsinates, $C_8$-$C_{22}$ taurates); and
  (v) mixtures thereof;

provided that the solubility enhancing components must be present in a minimum amount of at least 5 weight %;

(c1) 0.5-1.7 weight % of a hardening agent selected from the group consisting of inorganic electrolytes (especially sodium chloride), propylene glycol, mixtures of sodium chloride with polyethylene glycol (for example, PEG-600), and mixtures of sodium chloride with at least one high melting point wax (for example, 40-60° C. as a melting point range) (with a particular hardening agent being sodium chloride, especially in an amount of 1.1% sodium chloride);

(d1) 0.1-5 weight % of one or more of a $C_{12}$-$C_{20}$ straight or branched chain fatty acid (particularly coconut or stearic acid) (particularly 1.5% of coconut or stearic acid);

(e1) water (for example, 14-19 weight %); and (f1) optionally one or more ingredients selected from the group consisting of
- (i) an opacifying and/or pearlizing agent such as in an amount of 0-0.5 weight % of titanium dioxide, mica, coated mica, and mixtures thereof (particularly titanium dioxide such as in an amount of 0.3%);
- (ii) fragrance (such as in an amount of 0-2 weight %, particularly 1.2%);
- (iii) a preservative such as in amount of 0.02-0.1 weight % (particularly a chelating type of preservative such as pentasodium pentate or EDTA, especially 0.05% of pentasodium pentate);
- (iv) an antioxidant, for example in an amount of 0.01-0.05, particularly tetradibutyl pentaerythrityl hydroxyhydrocinnamate or butylated hydroxytoluene ("BHT"); particularly 0.02% of tetradibutyl pentaerythrityl hydroxyhydrocinnamate;
- (v) a colorant, for example in an amount of 0.001-0.1 weight %, particularly 0.002%;
- (vi) 0.01-5 weight % of a skin conditioner, for example one or more members selected from the group consisting of petrolatum, mineral oil, silicones, natural oils (such as sunflower, olive, jojoba, sesame, almond, safflower, wheat germ, canola or avacado oils), shea butter, lanolin, vitamin E, and mixtures thereof; and
- (vii) exfoliating agents, for example polyethylene beads, jojoba beads, oat flour, lufa or bran.

wherein the amounts in each of A and B portions are based on each separate portion as 100%.

The bar must contain at least two different portions, but it can contain additional portions, each with its own solubility profile, provided that the bar contains at least two portions that have a difference in solubility when used with water. Normally after standard use-up test this will translate to a height difference in a bar of 2.5 cm size thickness (approximately 100 grams) of at least 0.1 mm, particularly in the range of 0.1-0.6 mm. For example, the initial shape of the bar may be a rectangular bar 10 cm×6 cm with a thickness of 2.5 cm of thickness at its midpoint with some rounding at the edges.

In using the bars of this invention, ridges or areas of varying depth are created as the bar is used, thereby giving a textured bar, for example, with ridges only or a combination of ridges and regular or random areas of varying height on the bar that may be useful for a massaging and, optionally, an exfoliating effect.

In using the bars made according to Examples 1A and 1B, a difference in ridges was noticed as soon as 30 seconds after washing with the bar.

The bars of this invention may be of varying sizes and shapes such as ovoid or rectangular in shape with either a flat or curved profile as an overall appearance. For example, a rectangular bar 10 cm×6 cm with a thickness of 2.5 cm of thickness at its midpoint with some rounding at the edges. It is to be noted that in various embodiments of the invention, the initial surface of the bar may be either smooth or initially have some texture formed during the extrusion and/or pressing of the bar. During use, the smooth bar will develop appropriate ridges and the non-smooth bars will be able to have their texture enhanced. It should be noted that the difference in solubilities is critical to keep an initially non-smooth bar from wearing into a smooth one.

The bars may be made by the standard method of refining soap chips. For each portion the ingredients are weighed out on calibrated scales and mixed properly using an amalgamator or other mixing means. For each of the separate portions to be used, the separate portion mixed batch is preferably refined at least two times in an extruder or rolling mill. After both portions are refined the portions will then be processed using co-extrusion equipment (for example, combining the two portions when a bar is made that contains only the two portions to be made). This equipment includes two separate pieces of extrusion equipment joined together by a common co-extrusion nozzle that combines the two streams of soap into a distinct striped pattern. The striped pattern can be varied by the design of the co-extrusion nozzle insert. In one particular method (which comprises equipment used in the Examples), the dual extrusion equipment used includes the Twin Worm Mazzoni and Single Worm Mazzoni manufactured by Mazzoni LB in Italy. The common co-extrusion nozzle was also manufactured by Mazzoni LB in Italy. For example, Portion A is processed through the Single Worm Mazzoni and Portion B is processed through the Twin Worm Mazzoni; however, each of Portion A and Portion B can also be processed on the other extrusion equipment. The two streams are combined in the common co-extrusion nozzle, extruded, and then the soap billets are collected. The soap billets are pressed into soap bars on the soap press using conventional techniques known in the soap making art. The co-extrusion equipment is run under appropriate conditions of speed and temperature (for example, a speed in the range of 300-500 grams of soap per minute and a temperature in the range of 32-50° C.), particularly under a vacuum, for example, a vacuum of 500-600 mm Hg, to obtain the striped bars.

EXAMPLES

The following Examples are offered as illustrative of the invention and are not to be construed as limitations thereon. In the Examples and elsewhere in the description of the invention, chemical symbols and terminology have their usual and customary meanings. Temperatures are in degrees C unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7th ed. 1997).

Example 1A

A Bar Can Be Made Comprising:

Portion A—Less Soluble Portion:

82.6 weight % sodium soap (80/20 tallow/coco)

2.3 weight % glycerin 1.2 weight % fragrance 1.1 weight % stearic/coco fatty acid 0.7 weight % sodium chloride 0.3 weight % titanium dioxide
0.05 weight % pentasodium pentatate
0.02 weight % tetradibutyl pentaerythrityl hydroxyhydrocinnamate (contained in the fragrance)
0.002 weight % colorants
11.728 weight % water Portion B—More Soluble Portion:
65.5 weight % sodium soap (80/20 tallow/coco)
7.6 weight % glycerin
1.2 weight % fragrance
1.5 weight % stearic/coco fatty acid
1.1 weight % sodium chloride
5.7 weight % sorbitol
0.05 weight % pentasodium pentatate
0.02 weight % tetradibutyl pentaerythrityl hydroxyhydrocinnamate (contained in the fragrance)
0.002 weight % colorants
17.328 weight % water For Example 1A, the bars may be made by the standard method of refining soap chips. For each portion the ingredients are weighed out on calibrated scales and mixed properly. For each portion, the glycerin, stearic/coco fatty acid, sodium chloride, (sorbitol for portion B), (titanium dioxide for portion A), pentasodium pentatate, and water are already formulated into the soap chips along with the sodium soap. For each of the separate portions to be used, the separate portion mixed batch was refined two times in an extruder. After both portions were refined the portions were then processed using co-extrusion equipment (for example, combining the two portions when a bar is made that contains only the two portions to be made). This equipment includes two separate pieces of extrusion equipment joined together by a common co-extrusion nozzle that combines the two streams of soap into a distinct striped pattern. The striped pattern can be varied by the design of the co-extrusion nozzle insert. The dual extrusion equipment used included the Twin Worm Mazzoni and Single Worm Mazzoni manufactured by Mazzoni LB in Italy. The common co-extrusion nozzle was also manufactured by Mazzoni LB in Italy. Portion A was processed through the Single Worm Mazzoni and Portion B was processed through the Twin Worm Mazzoni; however, each of Portion A and Portion B can also be processed on the other extrusion equipment. The two streams were combined in the common co-extrusion nozzle, extruded, and then soap billets were collected. The soap billets were pressed into soap bars on the soap press using conventional techniques known in the soap making art. The co-extrusion equipment was run under appropriate conditions of speed and temperature (for example, a speed of 300 grams of soap per minute and a temperature in the range of 37-44° C.), particularly under a vacuum, for example, a vacuum of 500-600 mm Hg, to obtain the striped bars.

Example 1B

A Bar Can Be Made Comprising:

Portion A—Less Soluble Portion:
82.5 weight % sodium soap (80/20 tallow/coco)
2.3 weight % glycerin
1.2 weight % fragrance
1.1 weight % stearic/coco fatty acid
0.7 weight % sodium chloride
0.3 weight % titanium dioxide
0.1 weight % Inducos 14/3 Blue (polyethylene beads)
0.05 weight % pentasodium pentatate
0.02 weight % tetradibutyl pentaerythrityl hydroxyhydrocinnamate (contained in the fragrance)
0.002 weight % colorants
11.728 weight % water Portion B—More Soluble Portion:
65.5 weight % sodium soap (80/20 tallow/coco)
7.6 weight % glycerin
1.2 weight % fragrance
1.5 weight % stearic/coco fatty acid
1.1 weight % sodium chloride
5.7 weight % sorbitol
0.05 weight % pentasodium pentatate
0.02 weight % tetradibutyl pentaerythrityl hydroxyhydrocinnamate (contained in the fragrance)
0.002 weight % colorants
17.328 weight % water For Example 1B, the bars may be made by the standard method of refining soap chips. For each portion the ingredients are weighed out on calibrated scales and mixed properly. For each portion, the glycerin, stearic/coco fatty acid, sodium chloride, (sorbitol for portion B), (titanium dioxide for portion A), pentasodium pentatate, and water are already formulated into the soap chips along with the sodium soap. For each of the separate portions to be used, the separate portion mixed batch was refined two times in an extruder. After both portions were refined the portions were then processed using co-extrusion equipment (for example, combining the two portions when a bar is made that contains only the two portions to be made). This equipment includes two separate pieces of extrusion equipment joined together by a common co-extrusion nozzle that combines the two streams of soap into a distinct striped pattern. The striped pattern can be varied by the design of the co-extrusion nozzle insert. The dual extrusion equipment used included the Twin Worm Mazzoni and Single Worm Mazzoni manufactured by Mazzoni LB in Italy. The common co-extrusion nozzle was also manufactured by Mazzoni LB in Italy. Portion A was processed through the Single Worm Mazzoni and Portion B was processed through the Twin Worm Mazzoni; however, each of Portion A and Portion B can also be processed on the other extrusion equipment. The two streams were combined in the common co-extrusion nozzle, extruded, and then the soap billets were collected. The soap billets were pressed into soap bars on the soap press using conventional techniques known in the soap making art. The co-extrusion equipment was run under appropriate conditions of speed and temperature (for example, a speed of 300 grams of soap per minute and a temperature in the range of 37-44° C.), particularly under a vacuum, for example, a vacuum of 500-600 mm Hg, to obtain the striped bars. The less soluble portion "A" contains polyethylene beads that provide an exfoliating benefit.

Example 2

Comparative Bar

A comparative or control bar is made which contains two portions that have same solubility in water (differ by less than 1%) but differ in color:

Portion A:
82.6 weight % sodium soap (80/20 tallow/coco)
2.3 weight % glycerin
1.2 weight % fragrance
1.1 weight % stearic/coco fatty acid
0.7 weight % sodium chloride
0.3 weight % titanium dioxide 0.05 weight % pentasodium pentatate
0.02 weight % tetradibutyl pentaerythrityl hydroxyhydrocinnamate (contained in the fragrance)
0.002 weight % colorants
11.728 weight % water Portion B:
82.6 weight % sodium soap (tallow, palm and/or coco)
2.3 weight % glycerin
1.2 weight % fragrance
1.1 weight % stearic/coco fatty acid
0.7 weight % sodium chloride
0.3 weight % titanium dioxide
0.05 weight % pentasodium pentatate
0.02 weight % tetradibutyl pentaerythrityl hydroxyhydrocinnamate (contained in the fragrance)
0.002 weight % colorants
11.728 weight % water For Example 2, the bars may be made by the standard method of refining soap chips. For each portion the ingredients are weighed out on calibrated scales and mixed properly. For each portion, the glycerin, stearic/coco fatty acid, sodium chloride, titanium dioxide, pentasodium pentatate, and water are already formulated in with the sodium soap and form what is called soap chips. For each of the separate portions to be used, the separate portion mixed batch was refined two times in an extruder. After both portions were refined the portions were then processed using co-extrusion equipment (for example, combining the two portions when a bar is made that contains only the two portions to be made). This equipment includes two separate pieces of extrusion equipment joined together by a common co-extrusion nozzle that combines the two streams of soap into a distinct striped pattern. The striped pattern can be varied by the design of the co-extrusion nozzle insert. The dual extrusion equipment used included the Twin Worm Mazzoni and Single Worm Mazzoni manufactured by Mazzoni LB in Italy. The common co-extrusion nozzle was also manufactured by Mazzoni LB in Italy. Portion A was processed through the Single Worm Mazzoni and Portion B was processed through the Twin Worm Mazzoni; however, each of Portion A and Portion B can also be processed on the other extrusion equipment. The two streams were combined in the common co-extrusion nozzle, extruded, and then the soap billets were collected. The soap billets were pressed into soap bars on the soap press using conventional techniques known in the soap making art. The co-extrusion equipment was run under appropriate conditions of speed and temperature (for example, a speed of 300 grams of soap per minute and a temperature in the range of 37-44° C.), particularly under a vacuum, for example, a vacuum of 500-600 mm Hg, to obtain the striped bars.

Example 3

Separate portions made for Portions A and B as described in Example 1A were tested using the following protocol for a standard use-up test. The procedure is as follows:
1. Weigh bars and record initial weights. Label soap dishes (preferably with drainage pans) for each sample and place each bar in appropriate dish.
2. Have people wash with the bars for 10 seconds each in 37.8° C. water, using whatever hand wash technique they would normally use at home. Space the washes approximately 30 minutes apart.
3. Bars are washed a total of 20 times.
4. Once the washes are completed, allow the bars to dry for 24 hours at room temperature in dry soap dishes. Take the final bar weights, and calculate use-up or wear rate as percent weight loss.

Solubility Data:

Based on standard use-up test, the solubilities were evaluated as follows:

Example 1-A

For Portion A (less soluble): 21.4% used after twenty 10 second washes
For Portion B (more soluble): 26.6% used after twenty 10 second washes Example 1-B For Portion A (less soluble): 19.3% used after twenty 10 second washes
For Portion B (more soluble): 24.6% used after twenty 10 second washes Example 4

Surface Rating Test A

A surface rating can be done to evaluate the surface profile of the bar products.

Instrumental Method:

Bars prepared according to Example 1A were evaluated under the use up conditions described in Example 3. Defined ridges could be felt and were observed in the bar. These were measured using an Optical Comparator at a depth of 0.35 mm. The depth range is 0.05-1.0 mm particularly 0.3-0.6 mm.

Example 5

Surface Rating Test B

A surface rating can be done to evaluate the surface profile of the bar products.

Tactile Grading:

A panel was completed where panelists were asked to rate the ridges on the bar made according to Example 1A compared with a bar made in Example 2, where similar compositions were used in both sides. Comparison was done after the standard use-up test from a test such as Example 3. Panelists provided an average rating of "3.4" to the bar in Example 1A and an average rating of "1" to the bar in Example 2.

Ratings:
1. Bar has a smooth surface. No ridges can be felt.
2. Bar has a slightly uneven surface. Very minor ridges can be felt.
3. Bar has a moderately uneven surface. Some ridges can be felt.
4. Bar has an uneven surface. Defined ridges can be felt throughout the bar.
5. Bar has a very uneven surface. Distinct ridges can be felt throughout the bar.

What is claimed is:
1. A soap bar comprising at least two different portions wherein the portions have a difference in solubility of at least about 1.0%, and wherein the differences in solubilities between the at least two different portions causes a ridged structure to be formed upon use of the bar, wherein
  I) a first portion comprises
    a) about 82.6 weight % sodium soap that is about 80% tallow and 20% coco, b) about 2.3 weight % glycerin,
c) about 1.2 weight % fragrance,
d) about 1.1 weight % stearic/coco fatty acid,
e) about 0.7 weight % sodium chloride,
f) about 0.3 weight % titanium dioxide,
g) about 0.05 weight % pentasodium pentatate,
h) about 0.02 weight % tetradibuty penterythrityl hydroxyhydrocinnamate,
i) about 0.002 weight % colorant,
j) about 11.728 weight % water; and II) a second portion comprises
a) about 65.5 weight % sodium soap that is about 80% tallow and 20% coco,
b) about 7.6 weight % glycerin,
c) about 1.2 weight % fragrance,
d) about 1.5 weight % stearic/coco fatty acid,
e) about 1.1 weight % sodium chloride,
f) about 5.7 weight % sorbitol,
g) about 0.05 weight % pentasodium pentatate,
h) about 0.02 weight % tetradibuty penterythrityl hydroxyhydrocinnamate,
i) about 0.002 weight % colorant,
j) about 17.328 weight % water.

2. A soap bar comprising at least two different portions wherein the portions have a difference in solubility of at least about 1.0%, and wherein the differences in solubilities between the at least two different portions causes a ridged structure to be formed upon use of the bar, wherein I) a first portion comprises
a) about 82.5 weight % sodium soap that is about 80% tallow and 20% coco,
b) about 2.3 weight % glycerin,
c) about 1.2 weight % fragrance,
d) about 1.1 weight % stearic/coco fatty acid,
e) about 0.7 weight % sodium chloride,
f) about 0.3 weight % titanium dioxide,
g) about 0.1 weight % polyethylene beads
h) about 0.05 weight % pentasodium pentatate,
i) about 0.02 weight % tetradibuty penterythrityl hydroxyhydrocinnamate,
j) about 0.002 weight % colorant,
k) about 11.728 weight % water; and II) a second portion comprises
a) about 65.5 weight % sodium soap that is about 80% tallow and 20% coco,
b) about 7.6 weight % glycerin,
c) about 1.2 weight % fragrance,
d) about 1.5 weight % stearic/coco fatty acid,
e) about 1.1 weight % sodium chloride,
f) about 5.7 weight % sorbitol,
g) about 0.05 weight % pentasodium pentatate,
h) about 0.02 weight % tetradibuty penterythrityl hydroxyhydrocinnamate,
i) about 0.002 weight % colorant,
j) about 17.328 weight % water.

\* \* \* \* \*